(12) United States Patent  
Edgar et al.

(10) Patent No.: US 9,302,966 B2
(45) Date of Patent: Apr. 5, 2016

(54) THERMOCHEMICAL PREPARATION OF MONOALCOHOLS FROM BIOMASS

(71) Applicant: PHILLIPS 66 COMPANY, Houston, TX (US)

(72) Inventors: Lotero Edgar, Cleveland, OK (US); Fjare A. Kristi, Ponca City, OK (US); Sughrue L. Edward, Bartlesville, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 0 days.

(21) Appl. No.: 14/750,581

(22) Filed: Jun. 25, 2015

(65) Prior Publication Data

US 2015/0376095 A1 Dec. 31, 2015

Related U.S. Application Data

(60) Provisional application No. 62/017,393, filed on Jun. 26, 2014.

(51) Int. Cl.
*C07C 29/60* (2006.01)
*C07C 29/17* (2006.01)
(52) U.S. Cl.
CPC .............. *C07C 29/60* (2013.01); *C07C 29/172* (2013.01)
(58) Field of Classification Search
CPC .............................. C07C 29/60; C07C 29/172

USPC .................................................. 568/903, 902
See application file for complete search history.

(56) References Cited

PUBLICATIONS

Subramani, Velu, A Review of Recent Literature to Search for an Efficient Catalytic Process for the Conversion of Syngas to Ethanol, Energy & Fuels, 2008, 814-839, 22, Center for Energy Technology, Research Triangle Institute, Research Triangle Park, North Carolina 27709, USA.
Crossley, Steven, Solid Nanoparticles that Catalyze Biofuel Upgrade Reactions at the Water/Oil Interface, Science Magazine, Jan. 1, 2010, 68-73, vol. 327.

*Primary Examiner* — Elvis O Price
(74) *Attorney, Agent, or Firm* — Phillips 66 Company

(57) ABSTRACT

A process for converting polyhydric alcohols to monoalcohols in a counter current column reactor with a metal based catalyst supported on a porous membrane coated over a tubular system that delivers hydrogen where a hydrocarbon (low polarity) liquid solvent is fed at the bottom of the column reactor and an aqueous liquid having polyhydric alcohols therein is fed into the top of the reactor such that the aqueous liquid flows countercurrent to the low polarity solvent liquid and further wherein the low polarity solvent liquid is less dense than the aqueous liquid such that the two liquids are subject to phase separation. Monoalcohols are formed by hydrogenolysis reactions of polyhydric alcohols on the metal catalyst. Monoalcohols phase separate from the aqueous phase to the hydrocarbon solvent. Monoalcohols are further separated from the organic solvent.

7 Claims, 1 Drawing Sheet

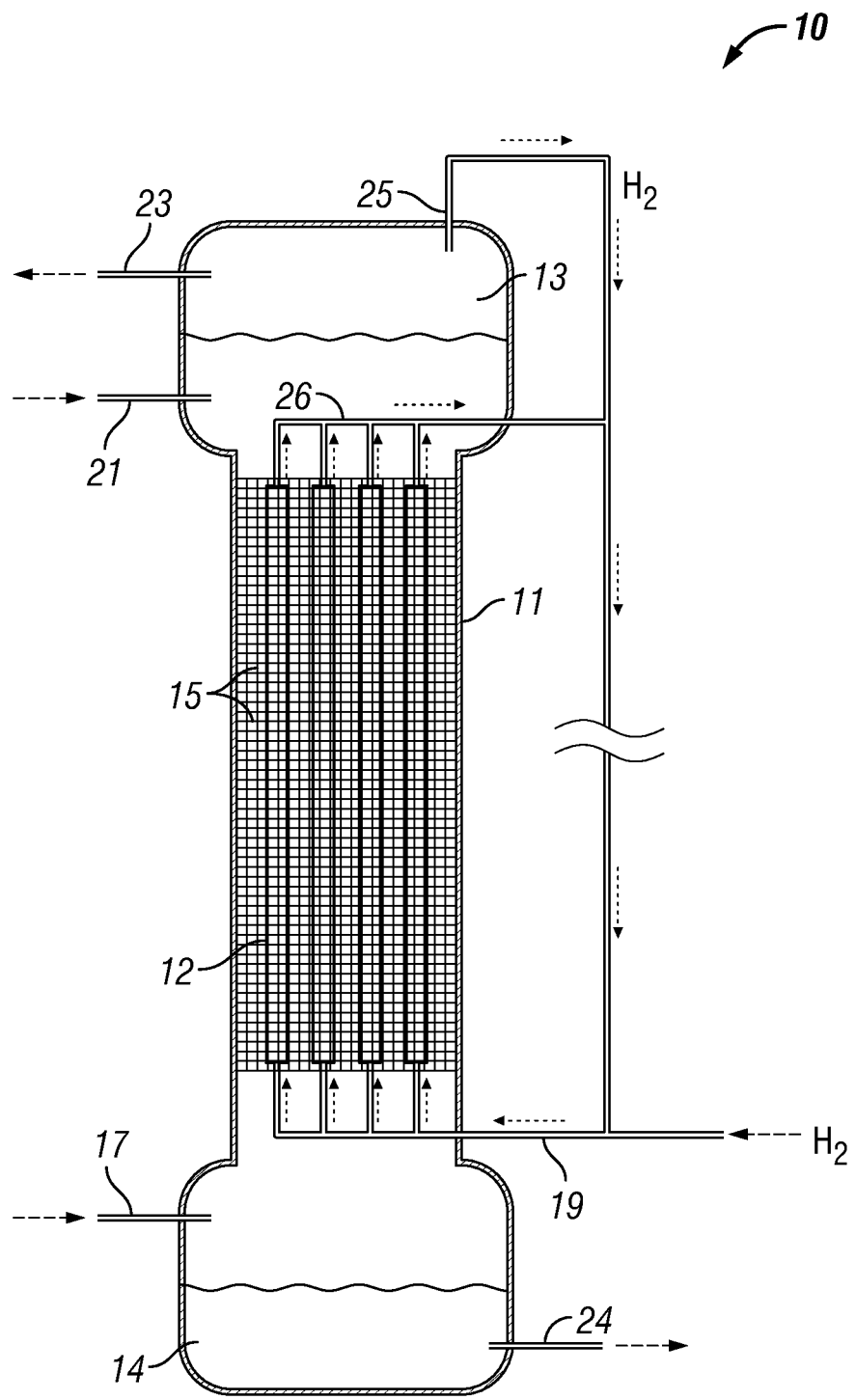

THERMOCHEMICAL PREPARATION OF MONOALCOHOLS FROM BIOMASS

CROSS-REFERENCE TO RELATED APPLICATIONS

This application is a non-provisional application which claims the benefit of and priority to U.S. Provisional Application Ser. No. 62/017,393 filed Jun. 26, 2014, titled "Thermochemical Preparation of Monoalcohols from Biomass," which is hereby incorporated by reference in its entirety.

STATEMENT REGARDING FEDERALLY SPONSORED RESEARCH OR DEVELOPMENT

None.

FIELD OF THE INVENTION

This invention relates to the creation or production of gasoline blendstock from biomass derived molecules and especially to the creation or production of alcohol gasoline blendstock that has a greater molecular weight so as not to be limited by the ethanol blendwall.

BACKGROUND OF THE INVENTION

Ethanol is the most well-known and commonly used biofuel around the world. It is directly used in blends with gasoline up to 10 volume to volume percent (v/v%) in the US. Blend ratios higher than 15% blends may cause unacceptable corrosion in both blending equipment and consumer cars that are not especially equipped to deal with this biofuel. This limitation is called the "blendwall". Biodiesel is also a well-known biofuel used as a diesel substitute. Some states in the US already require biodiesel/diesel blends of up to 2% biodiesel. Biodiesel, however, can present engine plugging problems when used at very low temperatures (winter) due to unfavorable cold flow properties. This biofuel can also present storage and stability problems. For example, fatty esters can undergo hydrolysis reactions increasing the acidity of the fuel and, hence, its corrosiveness. Due to the unsaturated nature of the hydrocarbon moieties in biodiesel, this biofuel also presents oxidative instability and bacterial growth can take place in biodiesel during long storage periods. As importantly, biodiesel viability is constrained by the current cost and availability of vegetable oils and animal fats used for its preparation. Due to governmental legislation requiring higher Renewable Fuels Standards (RFS), there is an increasing need for biofuels fungible at high concentrations with current transportation fuels.

Established biofuels, such as ethanol and biodiesel, present serious performance and stability problems. Mono-alcohols with 4-6 carbons are less problematic for fuel blend application since they show less of the corrosion issues associated with ethanol. These alcohols are more hydrophobic than ethanol; hence, they tend to absorb much less water. In addition, C4-C6 mono-alcohols have physicochemical properties closer to gasoline's and, because of their oxygen content; they still serve as octane enhancers. Thus, C4-C6 mono-alcohols will actually make better gasoline blending components than ethanol. However, there is a technology vacuum for the preparation of these alcohols from biomass in high volumes as required for their application as gasoline blending components in high concentrations.

Polyhydric alcohols (compounds with 2 or more hydroxyl groups) can be obtained by subsequent hydrolysis of biomass-derived carbohydrates and hydrogenation of the hydrolysis product. Two main technologies are used for carbohydrate hydrolysis, one technology is hydrothermal-hydrolysis with and without acid catalysis and the second is enzymatic hydrolysis. Enzymatic hydrolysis of carbohydrates produces sugars with high selectivity. Enzymes used for these purpose, however, are cost intensive and highly susceptible to reaction conditions (e.g., pH, temperature, water concentration, chemical inhibition, among other factors), losing their catalytic activity easily. Hydrothermal processing of carbohydrates can produce sugar in high yields, but also has a high tendency to form byproducts, i.e., sugar dehydration products, such as furfurals and levulinic acid. However, even such degradation products of sugars can be converted to polyhydric alcohols with subsequent hydrogenolysis processing. Hence, producing polyhydric alcohols is feasible and can be accomplished with current technology.

Producing mono-alcohols from polyhydric alcohols is challenging. Currently, fermentation of sugars is the main technology used for mono-alcohol synthesis for fuel applications. Fermentation technology has been extensively developed for ethanol production at a commercial scale. Presently, no other mono-alcohols are produced in high volumes from fermentation. Companies, such as BP and DuPont, and academic institutions, have focused their efforts on butanol production through fermentation with some success. Fermentation produces alcohol streams that require a large distillation operation to obtain water-free alcohols and can be energy intensive.

Currently, there is no commercial technology for the production of other fungible biofuels, such as mono-alcohols having between four and six carbon atoms such as butanols, pentanols, and hexanols, in volumes sufficient to compete with currently established biofuels.

There is an increasing desire to use abundantly available cellulosic materials as a source for biofuels.

BRIEF SUMMARY OF THE DISCLOSURE

The invention more particularly relates to a process for converting polyhydric alcohols to mono alcohols where a solvent is used that provides a low polarity phase separated from an aqueous phase liquid where the low polarity solvent phase is lighter than the aqueous phase. The low polarity solvent is fed at the bottom of a column reactor while the aqueous phase solution is fed at the top of the column reactor, so the low polarity solvent and aqueous liquid phase flow counter current to each other. A metal-based catalyst supported in a porous membrane is provided and it is located through the length of the column reactor. The membrane support where the metal-based catalyst is supported coats a tubular system from which a gas mixture containing hydrogen is injected at pressure. The injected hydrogen goes through the tubular system and disperses throughout the membrane and some of it adsorbs on metal sites and is activated for reaction. Reaction takes place between activated hydrogen on the metal catalytic sites and polyhydric alcohols in the aqueous liquid phase feed at the top of the column reactor. The c hydrogenolysis reaction removes excess hydroxyl groups in the polyhydric alcohol leading to the formation of monoalcohols. The whole column reactor is at a given temperature and pressure favoring hydrogenolysis while maintaining the reactor content in a liquid phase except for the hydrogen flowing through the tubular system. Once monoalcohols are formed through hydrogenolysis, monoalcohols migrate from the aqueous phase to the low polarity solvent phase. The low polarity solvent with monoalcohols is drawn from the top of the reactor and monoalcohols are separated from the solvent, which is reused in another reaction cycle. The aqueous phase depleted of polyhydric alcohols is drawn from the reactor from the bottom of the column. This phase is also cleaned from residual solvent and, when feasible, unreacted polyols and other polar oxygenates still in this phase are recycled and sent back for hydrogenolysis in the column reactor.

BRIEF DESCRIPTION OF THE DRAWINGS

A more complete understanding of the present invention and benefits thereof may be acquired by referring to the follow description taken in conjunction with the accompanying drawings in which:

FIG. 1 is diagram of a reactor system of the present invention.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The present invention provides a hydrothermal route to the production of mono-alcohols from biomass carbohydrates. The invention does not address the processing steps from biomass carbohydrates to polyhydric alcohols as those technologies have been developed or are being developed for cellulosic materials. It is believed that those technologies for cellulosics are coming and that the present invention fills a gap by converting polyhydric alcohols to mono-alcohols.

As shown in FIG. 1, a reaction system 10 which comprises a reactor 11 with a metal-based catalyst supported on a porous membrane coated over a tubular system 12 generally positioned in the middle of a column reactor 11 and spaced from the upper and lower ends thereof. The tubular system 12 is arranged to receive hydrogen at gas inlet 19.

A less dense hydrocarbon solvent is injected to the column reactor 11 via solvent inlet 17 at the bottom. This solvent is preferentially a hydrocarbon. In one embodiment, a mixture of hexanes, pentanes, and butanes constitute the solvent. In a different embodiment, gasoline is used as the solvent. Yet, in another embodiment, diesel is the organic solvent. An aqueous polyol or sugar feedstock solution is also injected to the reaction system at the top at aqueous phase inlet 21. Hence, both the hydrophobic solvent and the polyol solution are flowing within the column reactor in a countercurrent manner.

Due to the hydrophobic nature of the solvent and the polar nature of the aqueous feed, separation occurs between the solvent and the aqueous phase liquid. As good mixing between these two phases is preferred, the reaction system 10 is also equipped with a droplet forming media 15. Countercurrent separation columns with droplet forming systems are known and will not be discussed here. The porous membrane where the metal-based catalyst is supported coats a tubular system from which a gas mixture containing hydrogen is injected at pressure. The hydrogen is injected at gas inlet 19. The injected hydrogen goes through the tubular system and disperses throughout the membrane catalyst 12. The unreacted gas going through the column reactor may be recycled from vent 25.

As the gas passes through the membrane catalyst 12, hydrogen is activated for hydrogenolysis reactions with polyols in the aqueous media. The hydrogenolysis reaction removes hydroxyl groups in the polyols as water and replaces them with hydrogen. As the polyols lose their hydroxyl functionality, a point is reached where monoalcohols are formed. Monoalcohols with 4 to 6 carbons have great solubility in organic solvents and very low solubility in aqueous media. Hence, when a monoalcohol is formed it moves into the organic solvent where it is transported to the upper settling section 13 in the upper portion of the reactor 11 where the solvent is removed with monoalcohols at product outlet 23. The solvent is evaporated in a subsequent operation and recovered for further reuse leaving the desired monoalcohol product. The alcohols are then make ready for blending with the appropriate fuel for use in transportation applications.

As the reaction occurs throughout the column reactor 11, the aqueous phase is depleted of polyols and moves to the lower settling section 14 at the bottom of the reactor 11. The depleted aqueous phase is removed from the lower settling section 14 via aqueous phase outlet 24. This phase might be further treated to remove organic components, i.e., solvent and unreacted oxygenates.

Hydrogen gas that did not go through the membrane catalyst is collected flowing out of the membrane reactor system at collector 26. Non-reacted hydrogen that goes through the membrane reactor and into the two phase media is collected at the vent 25 at the top of the reactor 11. The non-reacted hydrogen stream is further cleaned and recycled through the gas inlet 19. The membrane reactors applied here are of different types, but particular success has been achieved with hollow fiber pervaporation membrane type. These membranes are loaded with a combination of metals suited for hydrogenolysis activity. With this type of reactor 11, hydrogen permeates into the membrane where it achieves intimate contact with the supported metals onto the membrane support. The liquid reactants that flow outside the membrane come into direct contact with the membrane metal coated surface with activated hydrogen and react via hydrogenolysis reactions. This approach eases mass transfer limitations that arise when hydrogen is injected external to the membrane. In this case, hydrogen has to dissolve into the liquid reacting media. Reactions with hydrogen in aqueous-liquid are especially challenging due to the very low hydrogen solubility in water, resulting in slow hydrogen diffusion to the catalyst surface. Under these conditions, the reaction is always hydrogen limited, requiring high pressures and temperatures that usually lead to undesired side reactions and expensive equipment needs.

Catalyst compositions include those that preferentially drive C—O bond hydrogenolysis. Compositions including Ru and Ru alloys are preferred for the application. Other suitable metals include Pt, Pd, Rh, Ir, and Re. In addition to using the right hydrogenolysis catalyst, the reaction can be conducted under mild conditions, i.e., 180° F. to 480° F., and preferentially 260° F. to 360° F. Pressures are usually in the range 40 psi to 2000 psi, and preferentially 200 psi to 1200 psi, and preferentially 300 psi to 600 psi.

There is a combination of principles that allows the reactor in FIG. 1 to work effectively. The polarity and density differences between the two liquid phases involved in the reaction allow a counter flow column reactor to be set up. Counter flow column reactors are easy to operate and low energy. A membrane support medium for the metal catalyst allows for a continuous mode of operation with no catalyst recycle. The membrane nature of the catalyst supports and the overall set up with hydrogen injection though the membrane permits for intimate contact between hydrogen and active metal centers with no need for hydrogen solubility in liquid medium and subsequent mass transfer limitations. The intimate contact of hydrogen and metal catalyst also allow for mild reaction conditions. Active and selective C—O hydrogenolysis catalyst that gradually, but efficiently, removes —OH functionality from polyols producing monoalcohols. Phase transfer of monoalcohols to a less polar hydrocarbon solvent that sequester monoalcohols and shelter them from further reaction. High boiling point difference between monoalcohols and organic solvent that permits the easy flashing of the solvent and separation from the monoalcohol product.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:
1. A Review of Recent Literature to Search for an Efficient Catalytic Process for the Conversion of Syngas to Ethanol. Subramani, Velu; Gangwal, Santosh K. Center for Energy Technology, Research Triangle Institute, Research Triangle Park, N.C., USA. Energy & Fuels (2008), 22(2), 814-839. Publisher: American Chemical Society, CODEN: ENFUEM ISSN: 0887-0624. Journal; General Review written in English. CAN 148:287869 AN 2008:120655 CAPLUS
2. Catalytic polymeric membranes: Preparation and application. Sibel Sain Ozdemir, Maria Giovanna Buonomenna, E. Driolib. Applied Catalysis A: General, Volume 307, Issue 2, 3 Jul. 2006, Pages 167-183
3. Overcoming Mass-Transfer Limitations in Partial Hydrogenation of Soybean Oil Using Metal Decorated Polymeric Membranes. Singh, D., Rezac, M., Pfromm, P. H., AIChE Journal, vol. 57(9), pg. 2450-2457, 2011.

The invention claimed is:

1. A process for converting polyhydric alcohols to monoalcohols where the process comprises:
    a) providing a counter current column reactor with a metal based catalyst supported on a porous membrane coated over a tubular system arranged to receive hydrogen;
    b) feeding a low polarity solvent liquid at the bottom of the counter current column reactor;
    c) feeding an aqueous liquid containing polyhydric alcohols into the top of the counter current column reactor such that the aqueous liquid flows countercurrent to the low polarity solvent liquid and further wherein the low polarity solvent liquid is less dense than the aqueous liquid such that the two liquids are subject to phase separation;
    d) injecting a hydrogen containing gas into the tubular system to disperse through the porous membrane;
    e) removing excess hydroxyl groups on the polyhydric alcohols in a hydrogenolysis reaction on the metal based catalyst to form monoalcohols;
    f) delivering the monoalcohols from the aqueous liquid to the low polarity solvent; and
    g) separating the produced monoalcohols from the low polarity solvent phase.

2. The process according to claim 1, wherein the process is operated at an elevated temperature and pressure favoring hydrogenolysis.

3. The process according to claim 1, wherein the low polarity solvent comprises at least one of hexanes, pentanes and butanes.

4. The process according to claim 1, wherein the metal based catalyst includes at least one of the following metals: Pt, Pd, Rh, Ru, Ir, and Re.

5. The process according to claim 1 wherein the aqueous liquid when depleted of polyhydric alcohols is removed from the column reactor and further treated to remove residual organic components such as solvent.

6. The process according to claim 5 wherein unreacted oxygenates remaining in the aqueous liquid are recycled to the counter current column reactor.

7. The process according to claim 1 wherein the low polarity solvent includes gasoline or diesel fraction hydrocarbons.

* * * * *